(12) United States Patent
Egan et al.

(10) Patent No.: US 6,174,324 B1
(45) Date of Patent: Jan. 16, 2001

(54) SUTURE GUIDE AND FASTENER

(75) Inventors: Thomas D. Egan, Marblehead; Daniel C. Taylor, Andover, both of MA (US)

(73) Assignee: Axya Medical, Inc., Beverly, MA (US)

( * ) Notice: Under 35 U.S.C. 154(b), the term of this patent shall be extended for 0 days.

(21) Appl. No.: 09/114,685

(22) Filed: Jul. 13, 1998

(51) Int. Cl.[7] .............................. A61B 17/04; B32B 31/16
(52) U.S. Cl. .......................... 606/232; 606/228; 156/73.1
(58) Field of Search ................................. 606/232, 233, 606/151, 148, 228; 156/73.1

(56) References Cited

U.S. PATENT DOCUMENTS

| | | | |
|---|---|---|---|
| 3,513,848 | * | 5/1970 | Winston et al. ...................... 606/228 |
| 4,662,068 | * | 5/1987 | Polonsky ................................. 301/24 |
| 5,593,425 | | 1/1997 | Bonutti et al. ....................... 606/232 |

* cited by examiner

*Primary Examiner*—Gary Jackson
(74) *Attorney, Agent, or Firm*—McDermott Will & Emery

(57) ABSTRACT

A suture guide and fastener includes a suture retaining device which orients and secures one or more suture strands therein and receives energy applied to the strands to bond them within the suture retaining device. The fastener becomes integral with the bonded sutures and may be made of a material similar to the suture material, which melts upon the application of energy thereto. Alternatively, the fastener may be made of a different material which remains intact upon application of bonding energy to the sutures. When ultrasonic energy is applied, the fastener may function as a stationary ultrasonic weld anvil. Other types of energy, such as laser, thermal or chemical, may be applied to the suture strands to effect bonding.

11 Claims, 5 Drawing Sheets

SUTURE GUIDE AND FASTENER

FIELD OF THE INVENTION

The invention relates to surgical suture fastening devices.

BACKGROUND OF THE INVENTION

In the surgical repair of soft tissue, such as, for example, the surgical reattachment of ligaments to bone or the attachment of tendon to muscle, it is known to use multi-part devices to surgically fasten the soft tissues to be repaired to the bone so as to avoid the use of knots. Suture knots are disadvantageous because they can be difficult to effect in tight spaces, they may not be uniformly tensioned and thus may slip or bind, and they can cause pressure on, or trauma to, surrounding tissue.

U.S. Pat. No. 5,593,425 to Bonutti et al. discloses surgical suture fastening devices which are assembled using a heat bondable material. The '425 patent teaches that a portion of a suture thread is inserted into an opening in a retainer formed of a plastic material having a melting point which is lower than the melting point of the suture material. At least one portion of the retainer is heated to its melting point. The plastic material of the retainer flows around the suture thread and creates a bond with the suture thread as the molten plastic material of the retainer cools below its melting point.

One disadvantage of the device disclosed in the '425 patent is that the surgeon must maintain tension on the retainer while simultaneously heat bonding the retainer to the suture, a sometimes difficult procedure. Another disadvantage of the Bonutti et al. device is that because the material of the retainer melts over the suture strands to encase them, instead of the suture material itself melting and bonding to itself, it may be difficult to control the geometry of the bond and/or the melting of the retainer and sutures, resulting in non-uniform coverage of the sutures by the melted material which flows around it.

It would therefore be an advantage to provide a suture fastening device that not only holds the strands of a suture thread together in preparation for bonding, but also effects melting of the suture strands within the device so that the sutures themselves are joined together and are not merely encased in a retainer which has been melted and cooled around them.

SUMMARY OF THE INVENTION

According to one aspect of the invention, there is provided a suture guide and fastener, comprising a suture retaining device adapted to receive one or more suture strands. This device includes:

i) means for orienting the suture strands within the device so that the suture strands are contiguous for at least a portion of their respective lengths within the device; and ii) means for receiving applied energy to the contiguous portion of the suture strands to effect bonding of the suture strands within the suture retaining device.

In a preferred embodiment, the means for orienting the suture strands includes guides for providing slidable insertion of the suture strands into and through the suture retaining device.

The fastener can further include means for retaining the suture strands in the device, preferably including one or more recesses in the suture retaining device. In a preferred embodiment, such a recess has a depth of at least two diameters of the suture strand, and a width of less than two diameters of the suture strand, whereby the suture strands in the recess are overlapped over at least a portion of their respective lengths. The device further preferably includes means for securing non-overlapping portions of the suture strands within the suture retaining device. The means for receiving applied energy preferably includes an opening in the suture retaining device which provides direct access to the suture strands therein, so that an energy source, such as an ultrasonic weld horn or laser or heat source, can be applied directly to the suture strands to bond them.

In an alternative embodiment, the means for retaining the suture strands in a contiguous orientation includes at least two recesses in the suture retaining device, each recess being adapted to receive a single suture strand. The suture strand contacing surfaces of the recess are preferably contoured to provide maximum contact area between the suture retaining device and the suture strands. In this embodiment, the suture retaining device encloses the suture strands, and energy is applied to an external surface of the suture retaining device.

The applied energy is preferably ultrasonic or thermal energy applied with, for example, an ultrasonic welding horn or a laser. If ultrasonic energy is applied, the suture retaining device preferably functions as a stationary ultrasonic weld anvil and holds one of the suture strands stationary relative to the other to create relative motion between them and cause localized melting of the suture strands as a result of frictional heating.

In one embodiment, the suture retaining device and the suture strands are preferably made of a material which melts upon application of ultrasonic energy thereto, whereby bonding is effected between the suture strands and the suture retaining device upon application of ultrasonic energy thereto.

In an alternative embodiment, the sutures only are made of a material which melts upon application of ultrasonic energy thereto, whereby bonding is effected between the suture strands within the suture retaining device upon application of ultrasonic energy thereto.

In another embodiment, the fastener can further include a suture thread fixedly attached at one end thereof to a portion of the suture retaining device.

BRIEF DESCRIPTION OF THE DRAWINGS

For a fuller understanding of the nature and objects of the present invention, reference should be made to the following detailed description taken in connection with the accompanying drawings, in which.

Like elements in the FIGURES have the same reference numerals.

DETAILED DESCRIPTION OF THE DRAWINGS

The fastener of the present invention combines several functions in a single- or multiple-piece suture retaining device which guides one or more suture strands into the device, and retains the suture strands in a desired orientation within the device so that energy applied either to the strands or to the device effects bonding of the strands to each other and/or to the suture retaining device.

The fastener is preferably in the form of a button- or tablet-shaped device with a nominal slot or recess in a top surface thereof. Its principal features include a tissue-contacting surface and a plurality of suture-contacting surfaces. The tissue-contacting surface provides an area for tissue contact that distributes the forces applied to the tissue through the suture, thereby minimizing trauma to the tissue at that location. The suture-contacting surfaces are designed to maintain and orient suture strands within the suture retaining device under a sufficient tension and with sufficient contact area to permit application of energy to the strands and bonding of the -strands to one another and/or to the surrounding suture retaining device.

Figure 1:
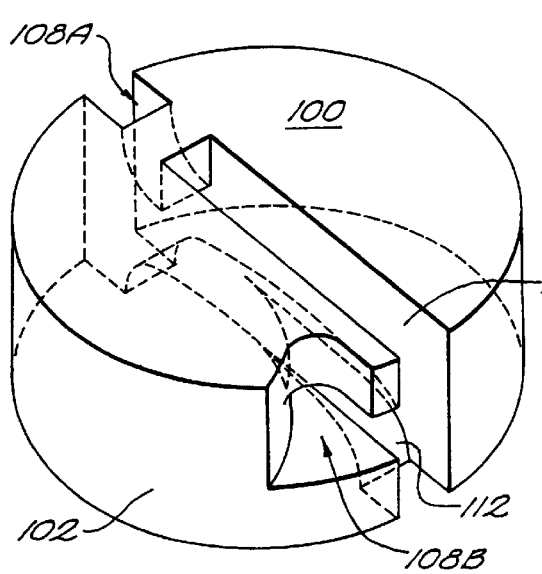
FIG. 1 is a perspective view of one embodiment of the fastener of the invention.
Figure 2:
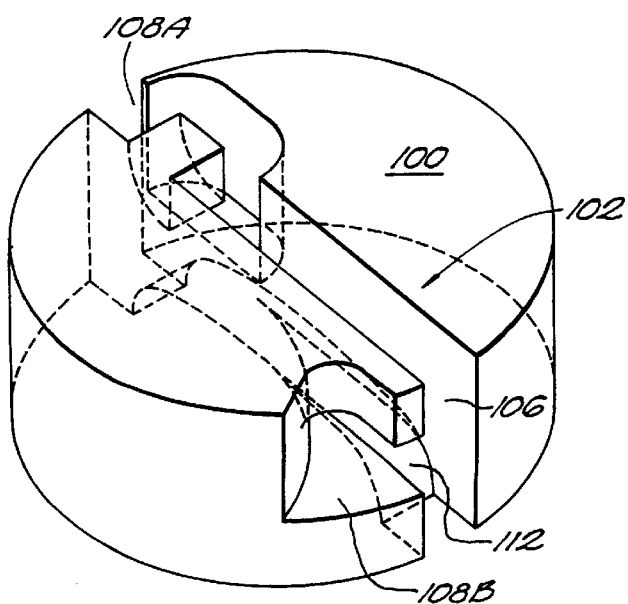
FIG. 2 is a perspective view of another embodiment of the fastener of the invention.

One embodiment of the fastener 100 is shown in FIG. 1, and a modified version of the fastener is shown in FIG. 2. The fastener in use with a suture deployed therein is shown in FIG. 3.

Figure 3:
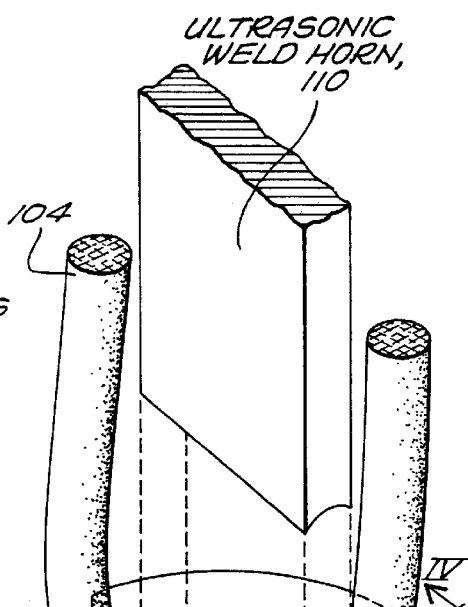
FIG. 3 is a perspective and partial cutaway view of the fastener of the invention, in which a suture has been threaded.
Figure 4:
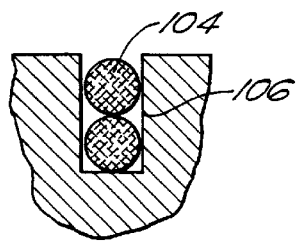
FIG. 4 is a sectional view of the fastener of FIG. 3, showing the overlapped orientation of the suture strands within the suture retaining device.

The fastener 100 includes a one- or multiple-piece suture retaining device 102 which is adapted to receive one or more suture strands 104, as most clearly shown in FIG. 3. The suture retaining device 102 orients the suture strands 104 so that they are at least contiguous, either adjacent to each other or overlapping, along a portion of their respective lengths, as provided for in the fastener of FIG. 1 and as shown in the sectional view of FIG. 4. Adjacent contiguous strand orientation is provided for in the fastener illustrated in FIG. 8.

The suture strands are retained in their contiguous or overlapping orientation in the suture retaining device by a series of slots 106 and guides 108, which may be contoured or otherwise adapted to permit sliding movement of the sutures therein and therethrough, so that the fastener can be moved along the suture strands to a desired position relative to bone and soft tissue to be fastened to the bone. In the embodiment of FIG. 1, guide 108A provides a U-shaped pathway for the suture strand to pass through, thereby providing some frictional engagement of the suture strand and the retaining device, even though sliding motion of the suture is permitted. Guide 108B at the opposite side of the retaining device permits a strand to exit the device without binding the portions of the suture to be bonded together. In the embodiment of FIG. 2, guide 108A is modified to permit drop-in insertion of the suture strand.

Figure 5:
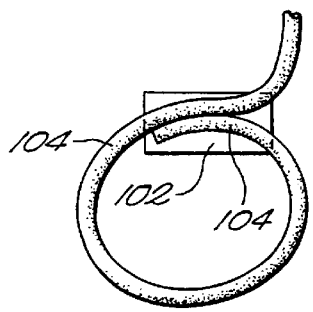
FIG. 5 is a side sectional view of the suture retaining device containing a suture, in which one end of the suture is fixed to the device.

FIG. 5 is a side view of a suture retaining device 102 to which is attached an end of a suture strand 104. This embodiment is advantageous because the fastener is provided with a suture already engaged to a portion of the retaining device, thereby preventing the use of sutures of a diameter which cannot be accommodated in the retaining device, or which are made of a material that cannot be bonded effectively with the energy applied to the device. As shown in FIG. 5, an end of one of the suture strands is affixed to the suture retaining device within one of the recesses, so that the free end of the suture strand can be positioned over the fixed end and bonded thereto or to the suture retaining device.

Figure 6:
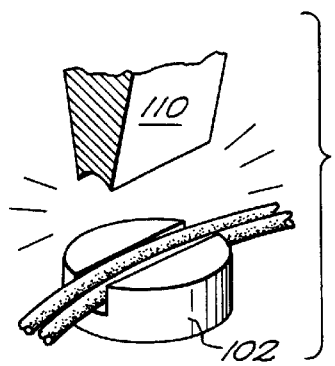
FIG. 6 is an exploded perspective view of another embodiment of the fastener of the invention, with suture strands in place and an ultrasonic weld horn positioned to apply energy directly to the suture strands.
Figure 7:
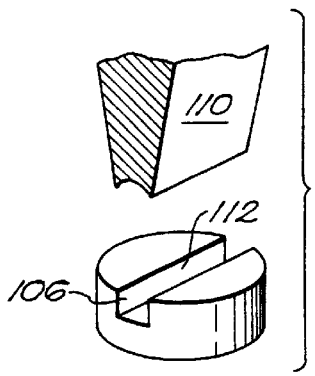
FIG. 7 is an exploded perspective view of the fastener of FIG. 6, without the suture strands inserted into the fastener, so that the suture recess can be seen.

FIGS. 6 and 7 illustrate a basic fastener with a single recess 112 for receiving one or more suture strands. FIGS. 1 and 2 represent variants of the fastener of FIGS. 6 and 7, in which the slots 106, guides 108 and recess 112 are positioned to receive and guide the non-contiguous portions of a suture strand as they enter and exit the suture retaining device. The slots 106 and recess 112 provide a fixed volume into which one or more suture strands 104 can be disposed within the device. The guides 108 provide entrance and exit pathways for the suture strands and function as frictional retainers for the suture strand ends so that they cannot easily disengage from the suture retaining device. In this way the suture strands are oriented properly within the suture retaining device and are maintained at a nominal tension prior to application of bonding energy thereto. The suture retaining device can have any type of internal geometry and surface texturing which would enhance the retention and tensioning of the suture strands therein, and the illustrated embodiments are merely exemplary.

Figure 8:
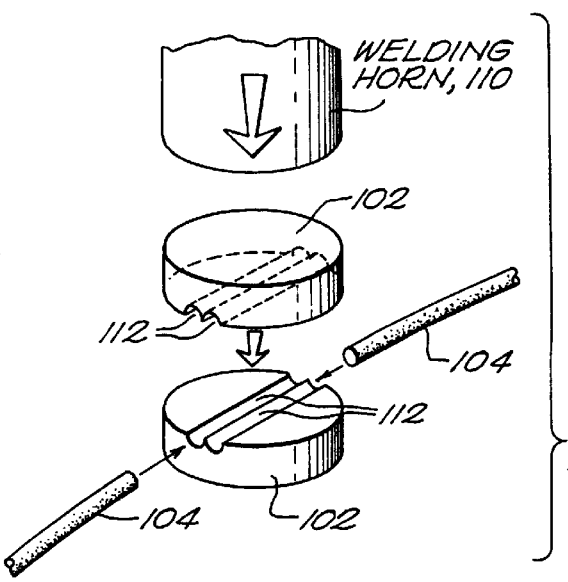
FIG. 8 is an exploded perspective view of a multi-part fastener and an ultrasonic welding horn positioned to apply energy to the fastener and sutures therein.
Figure 9:
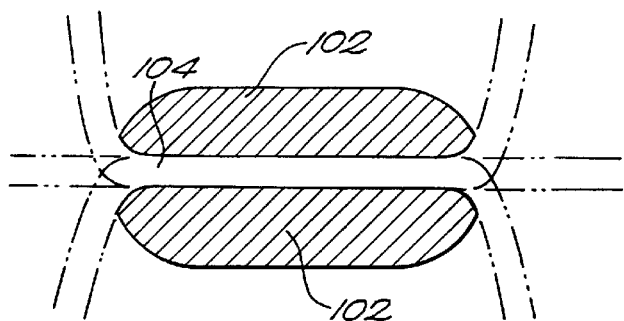
FIG. 9 is a side view of the fastener of FIG. 8, illustrating an advantageous geometry for the suture retaining device.
Figure 10:
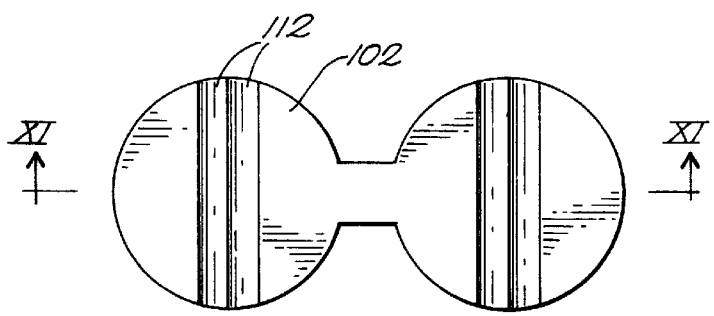
FIG. 10 is a plan view of another embodiment of the fastener, showing a single-piece construction with adjacent recesses or grooves for receiving suture strands therein.
Figure 11:
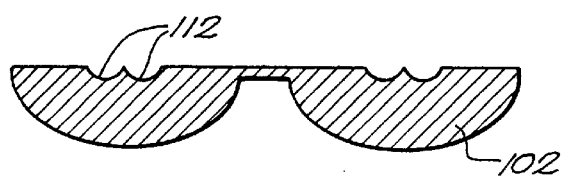
FIG. 11 is a sectional view of the fastener of FIG. 10.
Figure 12:
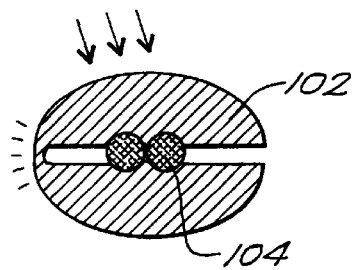
FIG. 12 is a side view of the fastener of FIGS. 10 and 11, with suture strands in place therein.

FIGS. 8–12 illustrate a variant of the fastener of FIGS. 6 and 7, in which at least two suture strand recesses 112 are positioned adjacent to one another so that the suture strands disposed therein are contiguous over a portion of their respective lengths. Each recess may have a depth of, for example, not greater than half the diameter of a single suture strand, although other geometries are considered to be within the scope of the invention. The suture retaining device 102 may be of a multiple-piece construction. Alternatively, the suture retaining device may be a single part which folds over itself, as shown in FIGS. 10–12, to enclose the suture strands 104 therein. Energy is applied to the suture retaining device itself instead of directly to the suture strands.

FIG. 9 illustrates some advantageous geometrical features of the fastener. All tissue- or suture-contacting edges of the suture retaining device 102 are preferably smoothly contoured so as to avoid any sharp discontinuities which could cut or damage a suture strand or segment of soft tissue. In addition, the recesses 112 are contoured for maximum contact with the suture strands therein, and the maximum length of suture-recess contact is preferred.

Energy is applied to the external surface of the device 102 with, for example, an ultrasonic weld horn 110, or a source of laser or thermal energy. Alternatively, an air- or energy-curable adhesive or epoxy may be applied to the suture strands and/or to the device surrounding the strands.

According to an important aspect of the invention, the suture retaining device 102 can function as a stationary ultrasonic weld anvil and transmits vibrational energy to the suture strands within it, thereby effecting relative motion between the strands and causing localized melting of the strands so as to create a molecular bond or weld between the suture strands. Alternatively, if the suture retaining device is made of a material similar to that of the suture strands, application of energy to the suture retaining device can cause it to melt with the suture strands, thereby effecting a bond between the suture strands and the retaining device.

Figure 13:
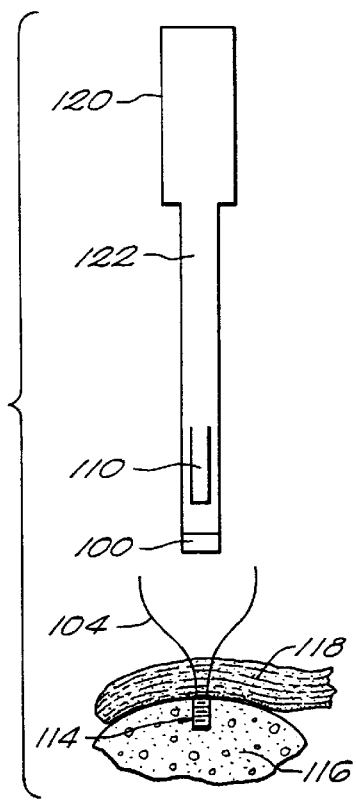
FIG. 13 is an exploded side view of an ultrasonic welding assembly being used with the fastener shown in FIG. 1 or 2 to secure soft tissue to a bone.
Figure 14:
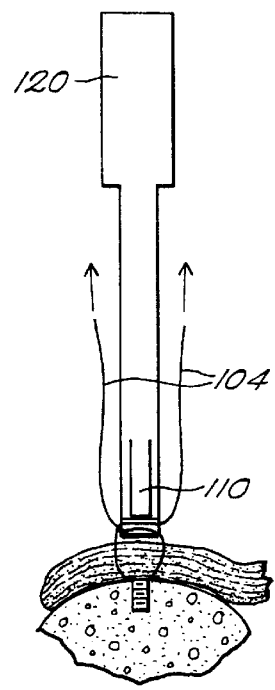
FIG. 14 is a side view of the ultrasonic welding assembly of FIG. 13 in operation.
Figure 15:
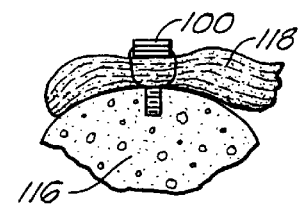
FIG. 15 is a side view of the fastener of FIGS. 13–14 bonded in place to secure the soft tissue to the bone.

FIGS. 13–15 illustrate the use of a fastener according to the invention. In FIG. 13, a suture anchor 114 for anchoring soft tissue to bone is installed into a bone 116. Strands of a suture 104 are threaded through an eyelet in the suture anchor and are passed through a segment of soft tissue 118. The ends of the suture strands are now ready to be fastened together with a fastener 100. In this embodiment, an ultrasonic weld horn 110 and transducer (not shown) are assembled into a deployment handle 120 including a shaft 122 that is adapted at its proximal end to selectively grip and release the fastener 100 by known means so as to position it in place over the soft tissue, and release it after ultrasonic energy has been applied to the fastener to bond the suture strands together.

In FIG. 14 the suture strands are loaded into the fastener 100. The deployment handle pushes the fastener 100 into place along the suture strands 104 to the soft tissue 118 and permits the suture strands to be tensioned appropriately in preparation for bonding. Ultrasonic energy is applied through the ultrasonic welding horn 110, and a bond is effected between the suture strands within the fastener. In FIG. 15 the deployment handle releases the fastener after bonding is completed so that the handle and welding horn can be removed. The bonded suture forms a loop extending through the soft tissue segment 118 and the bone anchor. The fastener 100 is now integral with the loop. The loose suture strand ends outside of the bond region can then be trimmed away.

Figure 16:
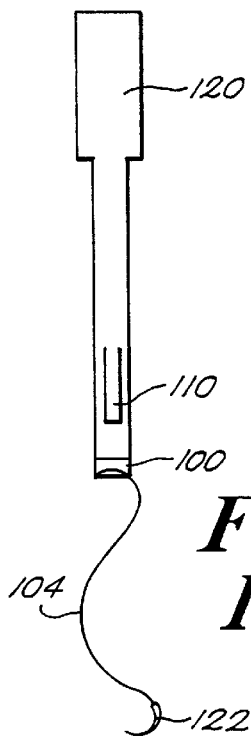
FIG. 16 is an exploded side view of an ultrasonic welding assembly with a fastener according to another embodiment of the invention.
Figure 17:
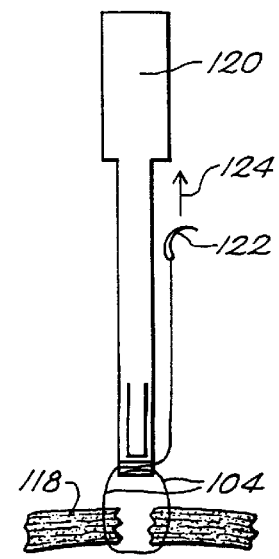
FIG. 17 is a side view of the ultrasonic welding assembly of FIG. 16 in operation.
Figure 18:
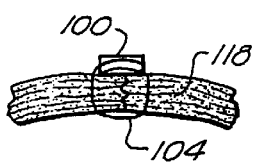
FIG. 18 is a side view of the fastener of FIGS. 16–17 bonded in place to secure the soft tissue to the bone.

FIGS. 16–18 illustrate another embodiment of the fastener in use. In FIG. 16, the fastener 100 is of the type which includes an attached suture 104. The suture 104 is prethreaded onto a surgical needle 122. The surgical needle 122 and suture 104 are threaded through the soft tissue 118 and tension is applied to the suture in the direction of arrow 124, shown in FIG. 17. In this embodiment, the fastener is positioned over the soft tissue segment, and ultrasonic energy is applied to the fastener 100 via the welding horn 110 to effect relative motion of the strands within the fastener, thereby causing the suture strands to bond together within the fastener.

Figure 19:
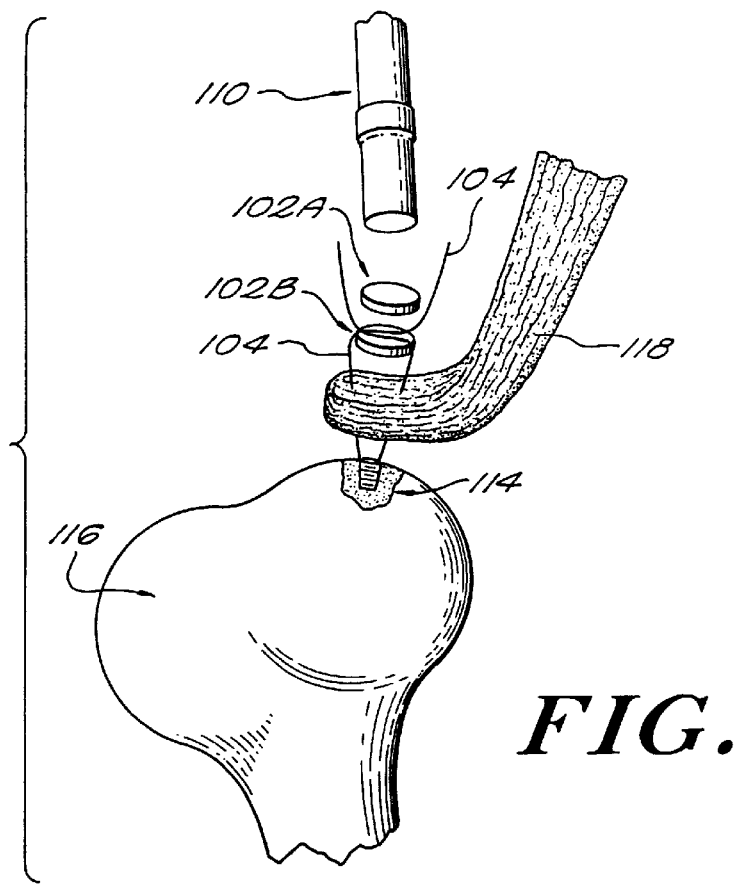
FIG. 19 is an exploded side view of an ultrasonic welding assembly with a fastener as shown in FIG. 8 or 12, before the suture strands are bonded within the fastener.
Figure 20:
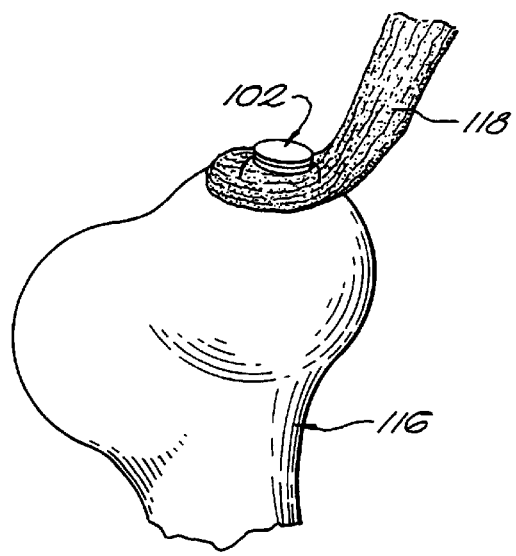
FIG. 20 is a perspective view of the fastener of FIG. 19 after the suture strands have been bonded therein.

FIGS. 19 and 20 illustrate the fastener of FIG. 8 in use. The fastener in this illustration has a two-piece suture retaining device, with a top piece 102A and a bottom piece 102B, with side-by-side recesses 112 in each piece. Each recess is sized to receive a single suture strand. The depth of each recess is preferably not greater than half the diameter of a suture to be used in the retaining device, and the recesses are adjacent to each other so that the portions of the suture strands disposed therein are contiguous. A bone anchor 114 is installed in a bone 116, and suture strands 104 are threaded through an eyelet in the anchor. The suture strands 104 are passed through a soft tissue segment 118 and placed within the recesses 112 of the bottom piece 102B of the suture retaining device, as shown in FIG. 19. The top piece 102A of the suture retaining device is then lowered onto the bottom piece to sandwich the suture strands 104 therein. In this embodiment, an ultrasonic weld horn 110 provides ultrasonic energy to the fastener and effects a bond between the suture strands therein. If the fastener is made of a material similar to that of the suture strands, it too may melt locally with the suture strands to form a bond between the suture strands and the fastener.

In all illustrations, the fastener 100 becomes an integral structure of the bonded suture loop and replaces a knot which would otherwise be formed at the location of the bond. In addition, the fastener acts as a non-abrasive, non-lacerating pledgit which distributes compressive force over an area of the soft tissue, thereby reducing suturing trauma and damage to the tissue. In addition, although the application of ultrasonic energy is illustrated, the invention is not limited to ultrasonic applications and can extend to, for example, application of thermal or chemical energy or even mechanical bonding agents to the suture strands and/or to the suture retaining device to form the bond.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description. All changes that come within the meaning and range of the equivalency of the claims are therefore intended to be embraced therein.

What is claimed is:

1. A suture guide and fastener, comprising:
    a suture retaining device in the form of a disk adapted to receive one or more suture strands, the disk including:
    i) means for orienting the suture strands within the device so that the suture strands are contiguous for at least a portion of their respective lengths within the device; and
    ii) means for receiving energy applied to the contiguous portion of the suture strands to effect bonding of the suture strands within the suture retaining device,
    wherein the sutures are made of a material which melts upon application of energy thereto, and wherein the suture retaining device is made of a material which does not melt upon application of energy to the sutures.

2. A suture guide and fastener according to claim 1, wherein the means for orienting the suture strands includes guide means for providing slidable insertion of the suture strands into and through the suture retaining device.

3. A suture guide and fastener according to claim 2, further comprising means for retaining received suture strands in a contiguous orientation, including a recess in the suture retaining device which has a depth of at least two diameters of the received suture strands, and a width of less than two diameters of the received suture strands, whereby received suture strands in the recess are overlapped over at least a portion of their respective lengths.

4. A suture guide and fastener according to claim 3, wherein the means for retaining the suture strands in a contiguous orientation includes at least two recesses in the suture retaining device, whereby each suture strand fits within a recess, and the suture strands in adjacent recesses are in partial contact with each other over at least a portion of their respective lengths.

5. A suture guide and fastener according to claim 3 or 4, wherein the suture strand-contacting surfaces of the recess are contoured to provide maximum contact area between the suture retaining device and the suture strands.

6. A suture guide and fastener according to claim 3 or 4, wherein the suture retaining device includes means for securing non-overlapping portions of the suture strands therein.

7. A suture guide and fastener according to claim 1, wherein the means for receiving applied energy includes an opening in the suture retaining device which provides direct access to the suture strands therein.

8. A suture guide and fastener according to claim 4, wherein the suture retaining device encloses the suture strands, and energy is applied to an exterior surface of the suture retaining device.

9. A suture guide and fastener according to claim 7 or 8, wherein the applied energy is ultrasonic energy applied with an ultrasonic welding horn, and wherein the suture retaining device functions as a stationary ultrasonic weld anvil.

10. A suture guide and fastener, comprising:
    a suture retaining device in the form of a disk adapted to receive two or more suture strands, the including:
    i) means for orienting received suture strands within the device so that the received suture strands are contiguous for at least a portion of their respective lengths within the device; and
    ii) means for receiving energy applied to the contiguous portion of the received suture strands to effect bonding of the suture strands within the suture retaining device, wherein the means for orienting the received suture strands includes guide means for providing slidable insertion of the suture strands into and through the suture retaining device, wherein the fastener further comprises means for retaining the suture strands in a contiguous orientation, including a recess in the suture retaining device which has a depth of at least two diameters of the received suture strands, and a width of less than two diameters of the received suture strands, whereby the suture strands in the recess are overlapped over at least a portion of their respective lengths, wherein the means for retaining the suture strands in a contiguous orientation includes at least two recesses in the suture retaining device, whereby each received suture strand fits within a recess, and the received suture strands in adjacent recesses are in partial contact with each other over at least a portion of their respective lengths, wherein the means for receiving applied energy includes an opening in the suture retaining device which provides direct access to the received suture strands therein, wherein the suture retaining device encloses the suture strands, and energy is applied to an exterior surface of the suture retaining device, wherein the applied energy is ultrasonic energy applied with an ultrasonic welding horn, and wherein the suture retaining device functions as a stationary ultrasonic weld anvil, wherein the received suture strands are made of a material which melts upon application of ultrasonic energy thereto, whereby bonding is effected between the suture strands within the suture retaining device upon application of ultrasonic energy thereto.

11. A suture guide and fastener according to claim 1, further comprising a suture thread fixedly attached at one end thereof to a portion of the suture retaining device.

* * * * *